United States Patent [19]

Hermann et al.

[11] 4,138,931
[45] Feb. 13, 1979

[54] PUMP

[75] Inventors: William G. Hermann, Arlington Heights; Manuel I. Martin, Hoffman Estates; Rolf Meyer, Des Plaines, all of Ill.

[73] Assignee: G. D. Searle & Co., Chicago, Ill.

[21] Appl. No.: 595,109

[22] Filed: Jul. 11, 1975

[51] Int. Cl.² .............................................. F01C 9/00
[52] U.S. Cl. ...................................... 92/87; 222/409; 417/399; 417/430
[58] Field of Search ............... 417/437, 430, 398, 400, 417/521, 399; 222/409, 333, 334, 137; 92/87

[56] References Cited

U.S. PATENT DOCUMENTS

| 1,599,625 | 9/1926 | Whitlock | 92/87 X |
| 2,952,386 | 9/1960 | Knights | 222/409 X |
| 3,019,739 | 2/1962 | Prosser | 92/168 |
| 3,050,002 | 8/1962 | Harris | 417/554 X |
| 3,160,331 | 12/1964 | Trumbull et al. | 222/409 X |
| 3,330,217 | 7/1967 | Baur et al. | 417/454 X |
| 3,800,984 | 4/1974 | Phelan | 222/137 X |

FOREIGN PATENT DOCUMENTS 716945  2/1942  Fed. Rep. of Germany ............. 92/168

Primary Examiner—Carlton R. Croyle
Assistant Examiner—Edward Look
Attorney, Agent, or Firm—Roy A. Ekstrand

[57] ABSTRACT

A hydraulic pump is provided which includes a plurality of housings, each of which has an upright cylindrical cavity formed therein, and a plurality of plungers, one for each cavity. The housings are removably mounted on a common support and the plungers are removably mounted on a common actuating member which is adapted to move in a linear path relative to the support and simultaneously move the plungers relative to the housing cavities.

3 Claims, 5 Drawing Figures

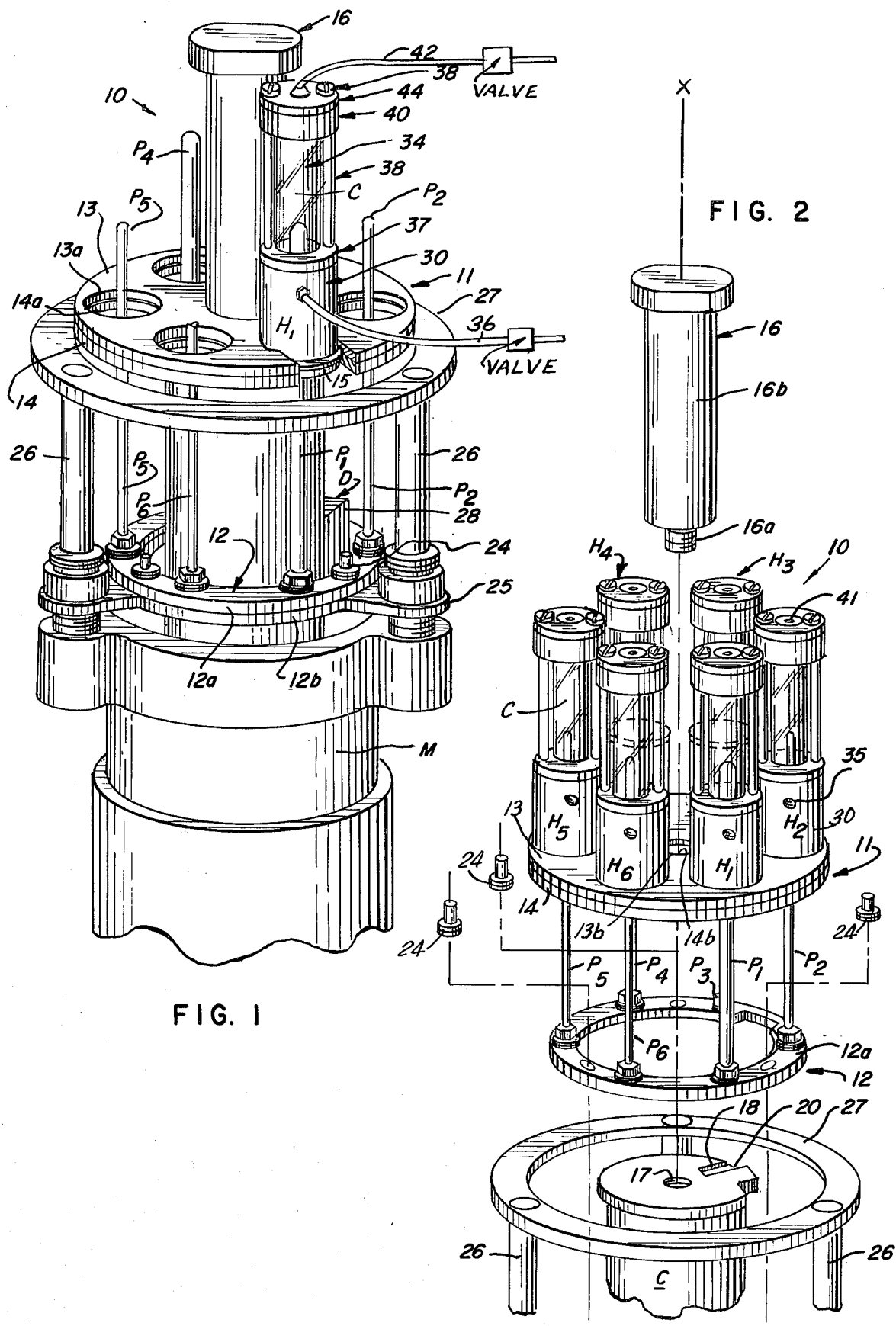

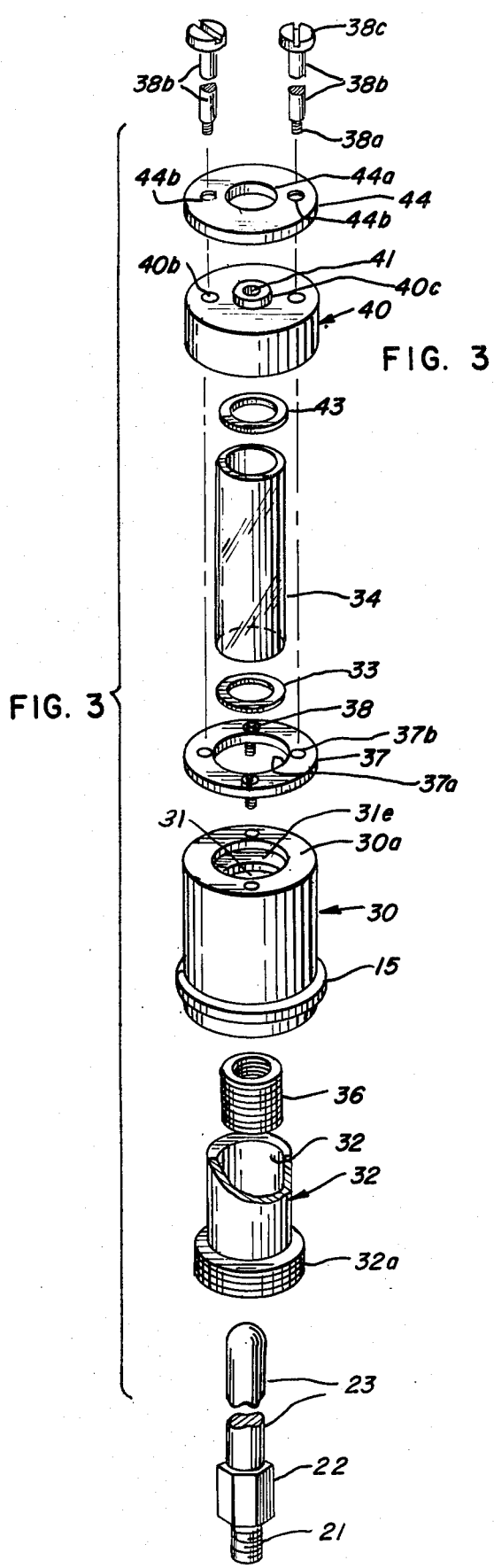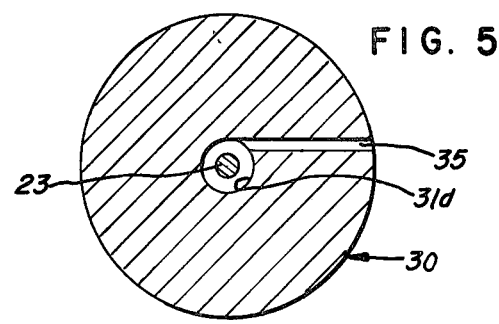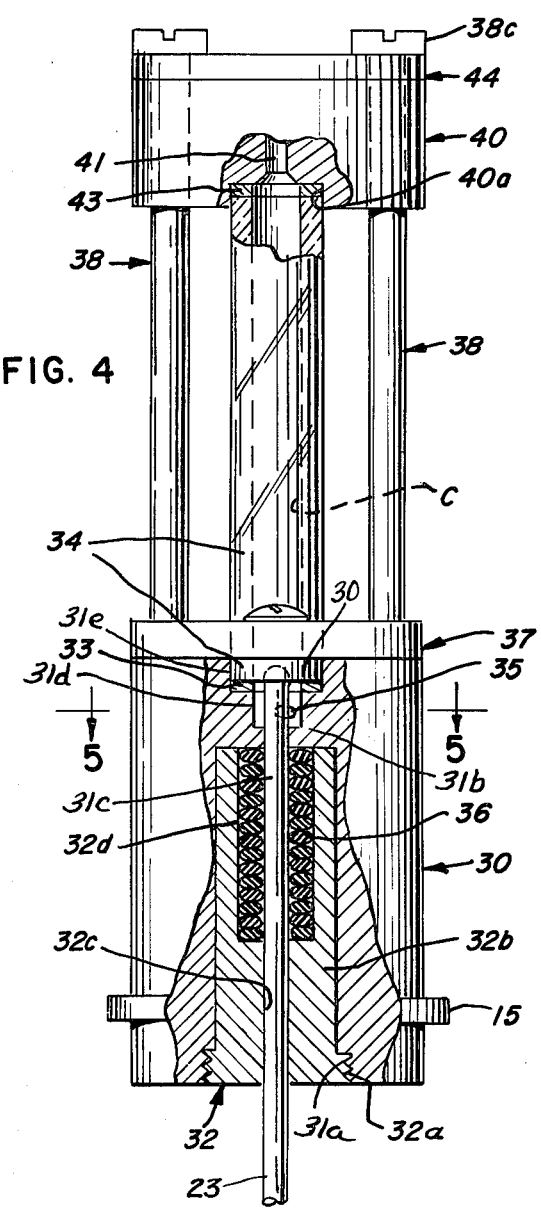

PUMP

BACKGROUND OF THE INVENTION

In sample preparation units, such as disclosed in pending application, Ser. No. 567,349 filed Apr. 11, 1975 now U.S. Pat. No. 4,000,976 it is desirable to utilize a pump which has the capabilities of simultaneously pumping numerous fluid samples into a plurality of individual receptacles disposed at predetermined stations. Because of rigid sanitary requirements to which such units are normally subjected, it is essential that the pump be readily disassembled for periodic cleaning. Furthermore, it is important that the seal means utilized in such a pump be easily replaced, when required, without necessitating substantial disassembly of the pump and/or resizing of the various components thereof. It is also desirable in a pump of this general type that the fluid flow within the pump interior produce a scrubbing effect on the surface defining the housing cavity and, thus, inhibit the formation of deposits or encrustations therein.

SUMMARY OF THE INVENTION

Thus, it is an object of the invention to provide a pump of the type described which is highly versatile for simultaneously pumping a plurality of fluids in like or variable amounts.

It is a further object of the invention to provide a pump of the type described wherein the fluid flow therethrough produces a scrubbing effect on the surface defining the housing cavity.

It is a further object of the invention to provide a pump of the type described which may be readily disassembled, when required, without the need for special tools or the talents of one possessed of a high degree of dexterity.

It is an additional object to produce a pump of the type described wherein the seal means embodied therein may be readily replaced with the disassembly of a minimal number of pump components.

It is another object of the invention to provide a pump of the type described wherein replacement of the seal means does not require resizing or realigning of various pump components.

It is still a further object of the invention to provide a pump of the type described wherein the formation and accummuluation of bubbles within the housing cavity are avoided.

Further and additional objects will appear from the description, accompany drawings, and appended claims.

In accordance with one embodiment of the invention, a hydraulic pump is provided which includes a plurality of housings removably mounted on common support. Each housing has a cylindrical cavity formed therein with longitudinally spaced inlet and outlet ports communicating therewith. A plurality of plungers are also provided (one for each housing cavity) which are slidably disposed within the cavities. The plungers are removably mounted on a common actuating member which, in turn, is mounted for controlled reciprocatory movement relative to the housing support. The inlet port for each cavity is positioned in a substantially tangential relation with respect to the cavity surface whereby fluid flow through the inlet port into the cavity, when the plunger is moving in one direction, produces a scrubbing effect on the cavity surface.

DESCRIPTION

For a more complete understanding of the invention, reference should be made to the drawings wherein:

FIG. 1 is a fragmentary, perspective view of one form of the improved pump and showing certain of the housings thereof removed from the support.

FIG. 2 is a fragmentary, perspective view of the pump of FIG. 1 but showing certain of the components thereof in exploded relation.

FIG. 3 is an exploded, perspective view of one of the housings shown in FIG. 2.

FIG. 4 is an enlarged, fragmentary, side elevational view partially in section of one of the housings shown in FIG. 2.

FIG. 5 is an enlarged, fragmentary sectional view taken along line 5—5 of FIG. 4.

Referring now to the drawings and more particularly to FIGS. 1 and 2, an improved hydraulic pump 10 is shown which is adapted to simultaneously pump a plurality of fluids. The pump 10 is of a type which may be readily embodied in a sample preparation unit, such as disclosed in the aforenoted pending application for United States patent. It is to be understood, of course, that pump 10 is not intended to be limited to use in such a unit.

In the illustrated embodiment, pump 10 includes a plurality of housings $H_1$, $H_2$, $H_3$, $H_4$, $H_5$, and $H_6$, all of which are of the same general construction and will be described more fully hereinafter. Associated with each housing is a corresponding plunger $P_1$, $P_2$, $P_3$, $P_4$, $P_5$, and $P_6$. The number of housings and plungers may be varied from that shown without departing from the scope of the invention herein desclosed.

The housings are symmetrically arranged about a vertical axis X and are removably mounted on a support 11. In a similar manner, the plungers are symmetrically arranged about the same axis and are removably mounted on an actuating member 12.

As seen in FIGS. 1, 2 and 3, the support 11 includes a pair of disc-shaped plates 13 and 14 which are arranged in superposed relation. The plates are provided with symmetrically arranged openings 13a and 14a. Corresponding openings are disposed in vertical alignment. Openings 13a are of like dimension and are adapted to conform substantially to the exterior configuration of the housings, except for an annular shoulder 15 formed on the exterior of each housing. Each of the openings 14a in plate 14 is countersunk from the upper surface of the plate an amount sufficient to accommodate the annular shoulder 15 of the corresponding housing. Thus, when the housings and plates are assembled, the housing shoulders will be clamped between the plates 13 and 14 and the housings retained in fixed upright positions.

Each plate is provided (see FIG. 2) with a central opening 13b and 14b which is adapted to accommodate the threaded shank 16a of a fastener 16. The shank is threaded into a suitable opening 17 formed in the upper end of a stationary column C, see FIG. 2. The upper end of column C is flat and engages the underside of plate 14. The exterior of column C is provided with a longitudinally extending slot 18 which is adapted to accommodate one component 20 of a sensing device D which will be described more fully hereinafter.

Fastener 16 is provided with an elongated head 16b which facilitates turning of the fastener when the housings are in place.

The ringlike member 12 is provided with a plurality of symmetrically arranged internally threaded openings which are adapted to receive the threaded end 21 (FIG. 3) of the respective plunger. The threaded end 21 of each plunger is of a standard size. To facilitate assembly and disassembly of the plunger from the member 12, each plunger has a facetted portion 22 adjacent end 21 which is adapted to accommodate the jaws of a wrench or similar tool.

Each plunger is of like construction and includes a rodlike portion 23 sized so as to slidably fit within a cavity C formed within the corresponding housing. The length of each rodlike portion 23 is preferably the same; however, the diameter thereof may be different and will depend upon the amount of fluid to be pumped per stroke of the plunger. In the illustrated embodiment, the diameters may vary from about one-sixteenth inch to about one half inch.

As seen in FIG. 1, ringlike member 12 includes an upper section 12a to which the plungers are affixed and a lower section 12b. The two sections are affixed to one another by suitable fasteners 24. Section 12b is provided with a plurality of apertured peripheral ears 25 which are adapted to slidably engage a corresponding number of stationary upright guide posts 26. The corresponding upper ends of the posts 26 are interconnected by a ring piece 27.

The actuating member 12 is mounted for reciprocatory movement and the movement thereof is effected by a linear type motor M, see FIG. 1. The operation of the motor is controlled by programming system, not shown. The length of the stroke of the plungers is primarily controlled by the sensing device D, previously referred to. Ring section 12a has mounted thereon a second component 28 (FIG. 1) of the sensing device D. Components 20 and 28 are adapted to cooperate with one another and transmit an impulse to the programming system indicating the extent to which the member 12 has moved towards support 11. A conventional microswitch or the like, not shown, may be mounted in a fixed position in the path of movement of the member 12 and be tripped thereby so as to interrupt the circuit to motor M and, thus, cause the latter to reverse its direction of operation. The microswitch may function as a safety feature and prevent overrun of the motor in one direction in the event of a malfunctioning of the sensing device D.

Because upper section 12a is removably mounted on section 12b, the upper section 12a may be readily replaced by a section in which the number and location of the plungers are different. In such a situation, the plates 13 and 14 of support 11 would also have to be replaced so as to assure proper disposition of the housings with respect to the plungers. FIGS. 3–5 disclose in greater detail the construction of the individual housings which are mounted on support 11. As aforementioned, each housing is of like construction except for the dimensions of the cavity C in which the plunger moves. As noted in FIGS. 3 and 4 particularly, the housing may be readily disassembled for cleaning or maintenance by merely removing a few fasteners. The housing includes a base portion 30 on which the exterior shoulder 15 is formed. The base portion 30 is provided with a central bore 31 through which the plunger extends. As seen in FIG. 4, the lower end segment 31a of bore 31 is enlarged and internally threaded so as to receive a seal-retainer element 32. Adjacent the lower end of bore 31 there is provided an inwardly extending annular shoulder 31b.

The opening 31c delimited by shoulder 31b conforms closely to the outside dimension of the plunger. Just above shoulder 31b, there is an enlarged bore section 31d. The upper end 31e of the bore 31 is countersunk so as to receive a seal ring 33 and the lower end of a sleeve 34 in which cavity C is formed. The central opening in seal ring 33, cavity C and bore section 31d have the same diameter.

As seen in FIGS. 4 and 5, base portion 30 is provided with an inlet port 35 which is connected at its outer end to suitable tubing 36 (FIG. 1). The inner end of port 35 communicates with bore section 31d in a substantially tangential manner, see FIG. 5. By reason of this arrangement between bore section 31d and port 35, the inflow of the fluid into bore section 31d produces a swirling or vortical motion to the fluid which, in turn, results in a scrubbing effect on the surface of the bore section, seal ring opening and the cavity C formed in sleeve 34.

Seal-retainer element 32, as seen in FIGS. 3 and 4, is of one-piece construction and includes an externally threaded end portion 32a which is adapted to engage the internally threaded bore section 31a. Extending axially from portion 32a is a sleeve-like shank portion 32b. The portions 32a and b are provided with a central opening 32c which is sized to substantially conform to the exterior dimension of the plunger. The upper end of opening 32c communicates with an enlarged cylindrical pocket 32d which is open at the lower end of shank portion 32b. When the retainer member 32 is assembled with the base portion 30 of the housing 12, the upper end of shank portion 32b will be in close proximity or abutting relation with shoulder 31b, see FIG. 4. Frictionally held within pocket 32d against base portion 30 are a plurality of annular seals 36 which are in sealing engagement with the exterior of the plunger when the housing and plunger are in assembled relation. Because of the lower end of pocket 32d being open and the seals 36 being frictionally held within the pocket, the replacement of one or more of the seals 36 can be readily accomplished by merely unthreading the member 32 from base portion 30, whereby the seals will be simultaneously withdrawn from base portion 30 because of the frictional engagement between the seals and the pocket surface. Once the retainer member 32 has been removed from the base portion 30 and the plunger disassembled from the housing (the latter being accomplished by freeing plate 13 from plate 14), the seals 36 may be readily removed through the open end of the pocket 32d. Once the seals 36 have been replaced in pocket 32d, the retainer 32, base portion 30 and plunger may be readily re-assembled. No resizing or realigning of the components are required. Furthermore, because the seals are only frictionally held within the pocket 32d, no special tools or techniques are required to remove the old seals from the retainer 32.

A cap ring 37 is provided which is secured by suitable fasteners 38 to the end face 30a of the base portion 30. Ring 37 is provided with a central opening 37a through which the lower end of sleeve 34 extends. In addition, ring 37 is provided with a pair of tapped holes 37b which are adapted to receive the threaded ends 38a of retainer bolts 38.

Disposed at the opposite or upper end of sleeve 34 is a cap piece 40 in which is formed the outlet port 41. The outer end of port 41 is connected to suitable tubing 42, see FIG. 1. The inner end of port 41 is recessed a slight amount so as to prevent contact between the upper end of the plunger rod when the plunger is disposed at the upper limit of its stroke. It is preferred that the inner end of the port 41 be disposed at the uppermost part of the cavity C so that any bubbles entrained in the flowing fluid will not accumulate and remain within the cavity C but will flow out through port 41.

A seal ring 43, similar to ring 33, is positioned along with the upper end of sleeve 34 in a recess 40a formed in cap piece 40. Holes 40b are formed in the cap piece 40 which are adapted to accommodate the shanks 38b of the bolts 38.

Overlying the upper end of cap piece 40 is a retainer ring 44 which is provided with a central opening 44a through which an exposed collar 40c extends. The collar 40c is formed on the upper surface of the cap piece 40 and surrounds the outer end of outlet port 41. Retainer ring 44 is also provided with holes 44b which are aligned with the holes 40b of cap piece 40 and thereby accommodate the shanks 38b of bolts 38.

Because base portion 30 and cap piece 40 may be formed of plastic material in which the size of an opening might vary slightly, the ring members 37 and 44 are preferably formed of metal in which threaded openings may be accurately formed, when required. The holes 44b are of such size that the heads 38c of the bolts 38 cannot pass therethrough. The cavity C formed in sleeve 34, the bore section 31d and the center openings in the seal rings 33 and 43, all cooperate to form a single cavity through which the fluid flows during operation of the pump.

Lastly, it will be appreciated that suitable valves of conventional design would be associated with the ports such as is schematically illustrated in FIG. 1, such valves being operated in association with the reciprocating movement of the plunger rod in typical fashion.

Thus, it will be seen that a pump has been provided which is highly versatile in simultaneously handling a plurality of fluids; is readily assembled and disassembled for cleaning and maintenance; is self-cleaning; and enables seals to be readily replaced without requiring special tools or extensive disassembly of the pump. The pump is directly driven by a conventional linear motor thereby materially simplifying the operation of the pump.

We claim:

1. A hydraulic displacement pump comprising an upstanding housing having a closed, elongated and substantially vertically disposed cylindrical cavity formed therein; an elongated rod of predetermined length and diameter constituting a plunger disposed through the lower end of said cylindrical cavity and axially upwardly at least partially into said cavity, means for effecting up and down reciprocating movement of said rod to displace liquid within said cavity; an outlet port disposed at the upper end of said cavity through which the liquid is discharged by upward movement of said rod; an inlet port disposed adjacent the lower end of said cavity and tangentially relative to the internal surface of said cylindrical cavity; means for supplying a fluid flow to said inlet port to thereby effect a swirling upwardly rising vortical motion of the fluid through the space between said axially elongated rod and the internal surface of said cylindrical cavity to scrub said internal surface and said rod; and valve means coupled with said inlet and outlet ports to effect selective opening and closing of same in association with the reciprocating movement of said rod.

2. The pump of claim 1 wherein the housing includes a removable seal-retaining member encompassing a portion of the reciprocating plunger, and seal means frictionally carried by said member and in sealing engagement with the plunger, said seal means being exposed and accessible for disassembly from said member when said member is removed from the remainder of the housing.

3. The pump of claim 2 wherein the seal-retaining member includes an elongated shank section provided with a central bore through which the plunger slidably extends; means at the outer end of said shank section for securing the member in assembled relation with the remainder of the housing.

* * * * *